(12) United States Patent
Euler

(10) Patent No.: US 7,200,438 B2
(45) Date of Patent: Apr. 3, 2007

(54) HIGH FREQUENCY ATRIAL BURST PACING FOR IMPROVED VENTRICULAR RATE CONTROL DURING ATRIAL ARRHYTHMIAS

(75) Inventor: David E. Euler, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 376 days.

(21) Appl. No.: 10/860,991

(22) Filed: Jun. 4, 2004

(65) Prior Publication Data

US 2006/0020293 A1 Jan. 26, 2006

(51) Int. Cl.
*A61N 1/368* (2006.01)

(52) U.S. Cl. ............................................ 607/14; 607/9
(58) Field of Classification Search ...................... None
See application file for complete search history.

(56) References Cited

U.S. PATENT DOCUMENTS

| | | | | |
|---|---|---|---|---|
| 4,316,472 A | 2/1982 | Mirowski et al. | ....... | 128/419 D |
| 4,375,817 A | 3/1983 | Engle et al. | ............ | 128/419 D |
| 4,384,585 A | 5/1983 | Zipes | .................... | 128/419 D |
| 4,577,633 A | 3/1986 | Berkovits et al. | ..... | 128/419 PG |
| 4,587,970 A | 5/1986 | Holley et al. | ......... | 128/419 PG |
| 4,726,380 A | 2/1988 | Vollmann et al. | ..... | 128/419 PG |
| 4,727,877 A | 3/1988 | Kallok | .................... | 128/419 D |
| 4,830,006 A | 5/1989 | Haluska et al. | ....... | 128/419 PG |
| 4,880,005 A | 11/1989 | Pless et al. | ........... | 128/419 PG |
| 4,949,719 A | 8/1990 | Pless et al. | ............. | 128/419 D |
| 5,117,824 A | 6/1992 | Keimel et al. | .......... | 128/419 D |
| 5,163,427 A | 11/1992 | Keimel | .................... | 128/419 D |
| 5,188,105 A | 2/1993 | Keimel | .................... | 128/419 D |
| 5,213,098 A | 5/1993 | Bennett et al. | | |
| 5,356,425 A * | 10/1994 | Bardy et al. | .................. | 607/14 |
| 5,411,524 A | 5/1995 | Rahul | ............................ | 607/4 |
| 5,620,468 A * | 4/1997 | Mongeon et al. | .............. | 607/5 |

(Continued)

FOREIGN PATENT DOCUMENTS

| | | |
|---|---|---|
| EP | 0748638 | 12/1996 |
| EP | 1304137 | 4/2003 |

OTHER PUBLICATIONS

Baeriswyl, G. et al., "Efficacy of Rapid Atrial Pacing for Conversion of Atrial Flutter in Medically Treated Patients," *Clin. Cardiol.*, vol. 17, p. 246-250 (1994).

(Continued)

*Primary Examiner*—Carl Layno
(74) *Attorney, Agent, or Firm*—Michael C. Soldner; Girma Wolde-Michael

(57) ABSTRACT

A method and device for delivering cardiac stimulation that includes a first electrode, positioned within a first chamber of a heart, sensing cardiac signals associated with the first chamber and capable of delivering stimulation to the first chamber, and a second electrode, positioned within a second chamber of the heart, sensing cardiac signals associated with the second chamber and capable of delivering stimulation to the second chamber. A processing unit processes the sensed signals and controls the stimulation delivery via the first electrode and the second electrode, determining whether a predetermined rhythm is detected in the first chamber, and delivering high-frequency burst pacing to the first chamber in response to a predetermined rate being sensed in the second chamber during the predetermined rhythm.

12 Claims, 4 Drawing Sheets

U.S. PATENT DOCUMENTS

| | | | |
|---|---|---|---|
| 5,792,193 A | 8/1998 | Stoop | 607/14 |
| 5,916,239 A | 6/1999 | Geddes et al. | 607/14 |
| 5,987,356 A | 11/1999 | DeGroot | 607/5 |
| 6,091,988 A | 7/2000 | Warman et al. | 607/5 |
| 6,249,703 B1 | 6/2001 | Stanton et al. | 607/30 |
| 6,434,424 B1 | 8/2002 | Igel et al. | 607/9 |
| 6,799,071 B2 | 9/2004 | Baker et al. | |
| 2003/0023272 A1* | 1/2003 | Shekhar et al. | 607/4 |
| 2003/0135242 A1* | 7/2003 | Mongeon et al. | 607/5 |
| 2004/0127946 A1* | 7/2004 | Wagner et al. | 607/5 |
| 2004/0220624 A1* | 11/2004 | Ritscher et al. | 607/4 |

OTHER PUBLICATIONS

Kowey, Peter R. et al., "Sustained Atrial Fibrillation as a Rhythm of Choice," *Circulation*, Abstract, vol. 60, No. 4, p. 11-253 (1979).

Winkle, Roger A., "Multifocal Atrial Tachycardia, Flutter, and Fibrillation," *Cardiac Arrhythmias: Current Diagnosis and Practical Management*, Addison-Wesley Publishing Company, p. 242 (1983).

Nabar, A. et al., "Radiofrequency Ablation of 'Class IC Atrial Flutter' In Patients With Resistant Atrial Fibrillation," *American Journal of Cardiology*, vol. 83, p. 785-787 (Mar. 1, 1999).

\* cited by examiner

HIGH FREQUENCY ATRIAL BURST PACING FOR IMPROVED VENTRICULAR RATE CONTROL DURING ATRIAL ARRHYTHMIAS

FIELD OF THE INVENTION

The present invention relates generally to implantable cardiac stimulation and monitoring devices and, more specifically, to a device and method for controlling delivery of cardiac stimulation.

BACKGROUND OF THE INVENTION

In the past, atrial arrhythmias have been largely undertreated due to the perception that these arrhythmias are relatively benign. As more serious consequences of persistent atrial arrhythmias have come to be understood, such as an associated risk of relatively more serious ventricular arrhythmias and stroke, there is a greater interest in providing implantable atrial or dual chamber cardioverter defibrillators for treating atrial arrhythmias.

Atrial fibrillation (AF) can be treated with relatively high voltage defibrillation shocks, which are generally painful to the patient, or high frequency burst pacing. Atrial flutter (AFL), also referred to herein as atrial tachycardia (AT) can be treated by anti-tachycardia pacing therapies, high frequency burst pacing or cardioversion shocks. Generally, it is preferred to initially treat AFL with a less aggressive therapy, such as anti-tachycardia pacing or burst pacing which are not painful to the patient and require less battery energy than cardioversion shocks. A tiered therapy approach is often taken in treating atrial arrhythmias, beginning with less aggressive therapies and, if these fail, progressing to more aggressive therapies.

Some patients experience persistent atrial arrhythmias that are refractory to arrhythmia therapies. Persistent AT or AF may be sustained continuously or return soon after being terminated. A persistent atrial arrhythmia may have undesirable effects on the ventricular rate. Relatively slow, organized AT is often accompanied by elevated ventricular rate. Methods proposed for controlling the ventricular rate during an atrial arrhythmia include ventricular pacing and vagal stimulation. See for example U.S. Pat. No. 5,792,193 issued to Stoop, U.S. Pat. No. 6,434,424 issued to Igel et al., and U.S. Pat. No. 5,916,239 issued to Geddes, et al.

A slowing of the ventricular rate has been observed clinically when AT is converted to AF. An opportunity may exist, therefore, for controlling the ventricular rate by accelerating the atrial rate during persistent atrial arrhythmias. While the primary goal in delivering arrhythmia therapies is to terminate an arrhythmia, there remains a need for controlling ventricular rate when persistent atrial arrhythmias remain refractory to arrhythmia therapies.

BRIEF DESCRIPTION OF THE DRAWINGS

Other aspects and features of the present invention will be readily appreciated as the same becomes better understood by reference to the following detailed description when considered in connection with the accompanying drawings, in which like reference numerals designate like parts throughout the figures thereof and wherein.

DETAILED DESCRIPTION OF THE PREFERRED EMBODIMENTS

The present invention provides a system and method for controlling ventricular rate during persistent atrial arrhythmias. In one embodiment, the method includes detecting an atrial arrhythmia; delivering programmed arrhythmia therapies; and, if the atrial arrhythmia therapies fail to terminate the arrhythmia and a fast ventricular rate is detected, delivering a selectable number of high frequency burst pacing sequences. If a slowed ventricular rate or an accelerated atrial rate is detected during the high-frequency burst pacing sequences, the burst pacing sequences may be suspended.

The present invention is realized in an implantable system including a cardiac stimulation device and associated leads equipped with electrodes for sensing the cardiac EGM signal. The device includes sensor interfaces and signal processing circuitry for determining cardiac rate information from the EGM signal. A control unit executes arrhythmia detection methods for detecting atrial arrhythmias. A therapy delivery unit delivers programmed atrial arrhythmia therapies in an attempt to terminate a detected atrial arrhythmia and delivers high-frequency burst pacing sequences when a slow atrial arrhythmia is associated with a fast ventricular rate.

Figure 1:
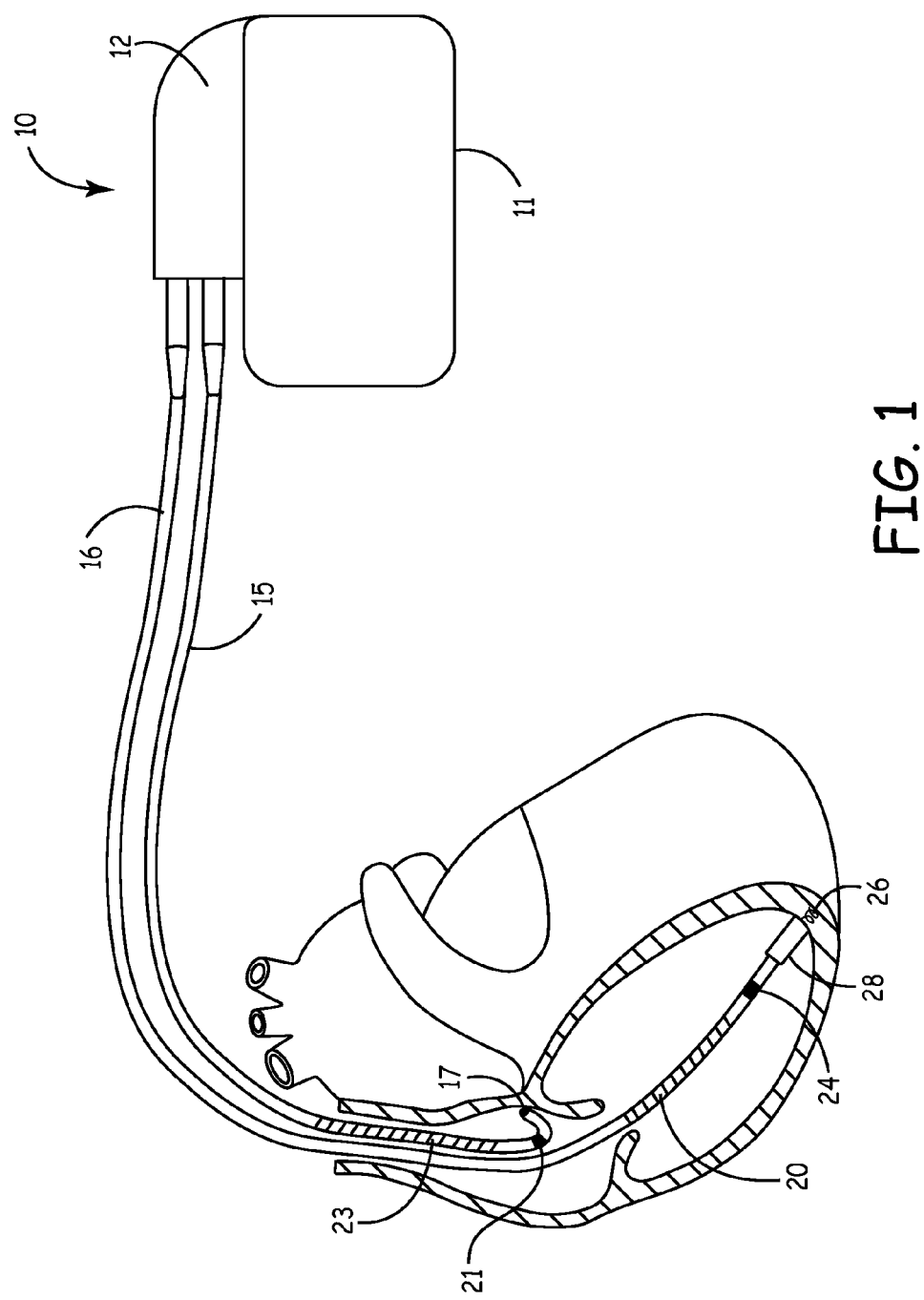
FIG. 1 is an illustration of an exemplary implantable cardiac stimulation device in which the present invention may be practiced.

FIG. 1 is an illustration of an exemplary implantable cardiac stimulation device in which the present invention may be practiced. Device 10 is provided with dual-chamber pacemaking, cardioversion, and defibrillation capabilities. Such dual chamber devices sense both atrial and ventricular events for the detection of arrhythmias in both atrial and ventricular chambers. The present invention may be embodied in a single, dual or multichamber cardiac stimulation device that includes at least atrial rate sensing, ventricular rate sensing, and atrial stimulation therapies and may or may not include ventricular stimulation therapies. Atrial stimulation therapy capabilities include at least high-frequency burst pacing and may include other anti-tachycardia pacing therapies, and/or higher voltage cardioversion/defibrillation pulses as well as bradycardia pacing or other pacing therapies. To illustrate the benefits of the present invention, the preferred embodiments described herein relate to a dual chamber implantable cardioverter defibrillator (ICD) device.

Device 10 of FIG. 1 is shown coupled to a patient's heart by way of a right atrial (RA) lead 15 and a right ventricular (RV) lead 16. A connector block 12 receives the proximal end of a right ventricular lead 16 and right atrial lead 15, used for positioning electrodes for sensing and stimulation. Right ventricular lead 16 is positioned such that its distal end is in the right ventricle (RV) for sensing right ventricular cardiac signals and delivering pacing or shocking pulses in the right ventricle. For these purposes, right ventricular lead 16 is equipped with a ring electrode 24, a tip electrode 26, optionally mounted retractably within an electrode head 28, and RV coil electrode 20, each of which are connected to an insulated conductor contained within the body of lead 16. The proximal end of the insulated conductors are coupled to corresponding connectors carried by a standard connector assembly at the proximal end of lead 16 for providing electrical connection to the device 10.

The right atrial lead 15 is positioned such that its distal end is in the right atrium. Lead 15 is equipped with a ring electrode 21 and a tip electrode 17 for sensing and pacing in the right atrium. Lead 15 is further equipped with a superior vena cava (SVC) coil electrode 23 for delivering high-energy shock therapy. The ring electrode 21, the tip electrode 17 and the SVC coil electrode 23 are each connected to an insulated conductor within the body of the right atrial lead 15. Each insulated conductor is coupled at its proximal end to a connector carried by a connector assembly.

The electrodes 17 and 21 or 24 and 26 may be used as bipolar pairs, commonly referred to as a "tip-to-ring" configuration, or individually in a unipolar configuration with the device housing 11 serving as the indifferent electrode, commonly referred to as the "can" or "case" electrode. The device housing 11 may also serve as a subcutaneous defibrillation electrode in combination with one or more of the defibrillation coil electrodes 20 or 23 for defibrillation of the atria or ventricles. It is recognized that alternate lead systems may be substituted for the lead system illustrated in FIG. 1. For example, the present invention may be practiced in ICD systems involving pace/sense and cardioversion/defibrillation electrodes deployed intracardially, intravenously, epicardially, submuscularly, and/or subcutaneously.

Figure 2:
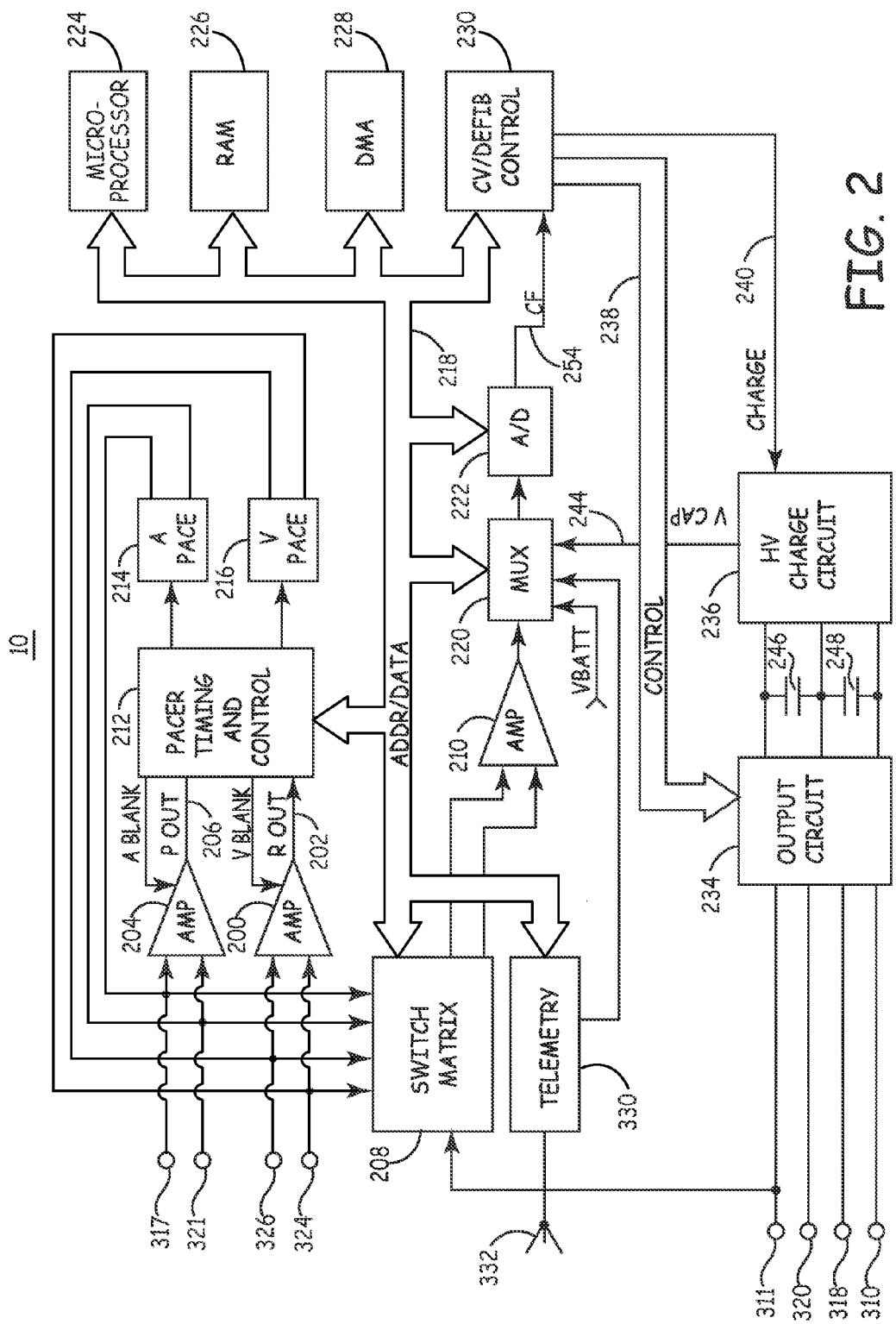
FIG. 2 is a functional block diagram of the cardiac stimulation device shown in FIG. 1.

FIG. 2 is a functional block diagram of the cardiac stimulation device shown in FIG. 1. This diagram should be taken as exemplary of the type of device with which the invention may be embodied and not as limiting, as it is believed that the invention may usefully be practiced in a wide variety of device implementations. For example, the disclosed embodiment shown in FIG. 2 is a microprocessor-controlled device, but the methods of the present invention may also be practiced with devices employing dedicated integrated circuitry for controlling device functions.

With regard to the electrode system illustrated in FIG. 1, the ICD 10 is provided with a number of connection terminals for achieving electrical connection to the cardiac leads 15 and 16 and their respective electrodes. The connection terminal 311 provides electrical connection to the housing 11 for use as the indifferent electrode during unipolar stimulation or sensing. The connection terminals 310 and 320 provide electrical connection to coil electrodes 20 and 23. Each of these connection terminals 311, 310, and 320, are coupled to the high voltage output circuit 234 to facilitate the delivery of high energy shocking pulses to the heart using one or both of the coil electrodes 20 and 23 and optionally the housing 11.

The connection terminals 317 and 321 provide electrical connection to tip electrode 17 and ring electrode 21 positioned in the right atrium. The connection terminals 317 and 321 are further coupled to an atrial sense amplifier 204 for sensing atrial signals such as P-waves. The connection terminals 326 and 324 provide electrical connection to tip electrode 26 and the ring electrode 24 positioned in the right ventricle. The connection terminals 326 and 324 are further coupled to a ventricular sense amplifier 200 for sensing ventricular signals.

The atrial sense amplifier 204 and the ventricular sense amplifier 200 preferably take the form of automatic gain controlled amplifiers with adjustable sensing thresholds. The general operation of the ventricular sense amplifier 200 and the atrial sense amplifier 204 may correspond to that disclosed in U.S. Pat. No. 5,117,824, by Keimel, et al., incorporated herein by reference in its entirety. Whenever a signal received by atrial sense amplifier 204 exceeds an atrial sensing threshold, a signal is generated on the P-out signal line 206. Whenever a signal received by the ventricular sense amplifier 200 exceeds a ventricular sensing threshold, a signal is generated on the R-out signal line 202.

Switch matrix 208 is used to select which of the available electrodes are coupled to a wide band amplifier 210 for use in digital signal analysis. Selection of the electrodes is controlled by the microprocessor 224 via data/address bus 218. The selected electrode configuration may be varied as desired for the various sensing, pacing, cardioversion and defibrillation functions of the ICD 10. Signals from the electrodes selected for coupling to bandpass amplifier 210 are provided to multiplexer 220, and thereafter converted to multi-bit digital signals by A/D converter 222, for storage in random access memory 226 under control of direct memory access circuit 228. Microprocessor 224 may employ digital signal analysis techniques to characterize the digitized signals stored in random access memory 226 to recognize and classify the patient's heart rhythm based on EGM information employing any of the numerous signal processing methods known in the art. EGM signal information is preferably employed for detecting atrial and ventricular rates for the purposes of the present invention, however, it is recognized that alternative signals, such as mechanical signals, may used for deriving cardiac rates and may be used in conjunction with the present invention in addition to or in place of electrical signals.

The telemetry circuit 330 receives downlink telemetry from and sends uplink telemetry to an external programmer, as is conventional in implantable cardiac stimulation devices, by means of an antenna 332. Received telemetry is provided to microprocessor 224 via multiplexer 220. Data to be uplinked to the programmer and control signals for the telemetry circuit 330 are provided by microprocessor 224 via address/data bus 218. Data to be uplinked may include a record of detected and classified arrhythmia episodes as is customary in modern implantable cardioverter defibrillators. Numerous types of telemetry systems known for use in implantable devices may be used.

The remainder of circuitry illustrated in FIG. 2 is dedicated to the provision of cardiac pacing, cardioversion and defibrillation therapies and, for the purposes of the present invention, may correspond to circuitry known in the prior art. In the exemplary embodiment shown in FIG. 2, the pacer timing and control circuitry 212 includes programmable digital counters which control the basic time intervals associated with various dual-chamber pacing modes or anti-tachycardia pacing therapies delivered in the atria or ventricles. Pacer circuitry 212 also determines the amplitude of the cardiac pacing pulses under the control of microprocessor 224.

During pacing, escape interval counters within pacer timing and control circuitry 212 are reset upon sensing of R-waves or P-waves as indicated by signals on lines 202 and 206, respectively. In accordance with the selected mode of pacing, pacing pulses are generated by atrial pacer output circuit 214 and ventricular pacer output circuit 216. The pacer output circuits 214 and 216 may be coupled to the desired electrodes for pacing via switch matrix 208. The escape interval counters are reset upon generation of pacing pulses, and thereby control the basic timing of cardiac pacing functions, including anti-tachycardia pacing.

The durations of the escape intervals are determined by microprocessor 224 via data/address bus 218. The value of the count present in the escape interval counters when reset by sensed R-waves or P-waves can be used to measure R—R intervals, P—P intervals, P–R intervals, and R–P intervals, which measures are stored in memory 226 and for use in diagnosing the occurrence of a variety of arrhythmias.

Microprocessor 224 operates as an interrupt driven device and is responsive to interrupts from pacer timing and control circuitry 212 corresponding to the occurrences of sensed P-waves and R-waves and corresponding to the generation of cardiac pacing pulses. Any necessary mathematical calculations to be performed by microprocessor 224 and any updating of the values or intervals controlled by pacer timing/control circuitry 212 take place following such interrupts. A portion of the random access memory 226 may be configured as a number of recirculating buffers capable of holding a series of measured intervals, which may be analyzed in response to a pace or sense interrupt by microprocessor 224 for diagnosing an arrhythmia. Any of the various arrhythmia detection methodologies known to the art may be employed in conjunction with the present invention for detecting and classifying arrhythmias.

In response to the detection of atrial flutter or ventricular tachycardia, an ATP therapy may be delivered if desired by loading a regimen from microcontroller 224 into the pacer timing and control circuitry 212 according to the type of tachycardia detected. Alternatively, circuitry for controlling the timing and generation of anti-tachycardia pacing pulses as generally described in U.S. Pat. No. 4,577,633 issued to Berkovits et al., U.S. Pat. No. 4,880,005 issued to Pless et al., U.S. Pat. No. 4,726,380 issued to Vollmann et al., and U.S. Pat. No. 4,587,970 issued to Holley et al, all of which patents are incorporated herein by reference in their entireties, may be used.

In the event that higher voltage cardioversion or defibrillation shock pulses are required, microprocessor 224 activates the cardioversion and defibrillation control circuitry 230 to initiate charging of the high voltage capacitors 246 and 248 via charging circuit 236 under the control of high voltage charging control line 240. The voltage on the high voltage capacitors 246 and 248 is monitored via a voltage capacitor (VCAP) line 244, which is passed through the multiplexer 220. When the voltage reaches a predetermined value set by microprocessor 224, a logic signal is generated on the capacitor full (CF) line 254, terminating charging. Thereafter, timing of the delivery of the defibrillation or cardioversion pulse is controlled by pacer timing and control circuitry 212.

One embodiment of an appropriate system for delivery and synchronization of ventricular cardioversion and defibrillation pulses and for controlling the timing function related to them is generally disclosed in commonly assigned U.S. Pat. No. 5,188,105 to Keimel, incorporated herein by reference in its entirety. If atrial defibrillation capabilities are included in the device, appropriate systems for delivery and synchronization of atrial cardioversion and defibrillation pulses and for controlling the timing function related to them may be found in U.S. Pat. No. 4,316,472 issued to Mirowski et al., U.S. Pat. No. 5,411,524 issued to Mehra, or U.S. Pat. No. 6,091,988 issued to Warman. Any known ventricular cardioversion or defibrillation pulse control circuitry may be usable in conjunction with the present invention. For example, circuitry controlling the timing and generation of cardioversion and defibrillation pulses as disclosed in U.S. Pat. No. 4,384,585, issued to Zipes, U.S. Pat. No. 4,949,719, issued to Pless et al., and in U.S. Pat. No. 4,375,817, issued to Engle et al., may be used in a device employing the present invention.

In the illustrated device, delivery of cardioversion or defibrillation pulses is accomplished by output circuit 234, under control of control circuitry 230 via control bus 238. Output circuit 234 determines the shock pulse waveform, e.g. whether a monophasic, biphasic or multiphasic pulse is delivered, whether the housing 311 serves as cathode or anode, which electrodes are involved in delivery of the pulse, and the pulse shape and tilt. Examples of high-voltage cardioversion or defibrillation output circuitry are generally disclosed in U.S. Pat. No. 4,727,877 issued to Kallok, and U.S. Pat. No. 5,163,427 issued to Keimel.

In modern implantable cardioverter defibrillators, the particular therapies are programmed into the device ahead of time by the physician, and a menu of therapies is typically provided. For example, on initial detection of tachycardia, an ATP therapy may be selected. On redetection of tachycardia, a more aggressive ATP therapy may be scheduled. If repeated attempts at ATP therapies fail, a higher-level cardioversion pulse therapy may be selected thereafter. As in the case of currently available ICDs, and as discussed in the above-cited references, the amplitude of the defibrillation shock may be incremented in response to failure of an initial shock or shocks to terminate fibrillation. Prior art patents illustrating such pre-set therapy menus of anti-tachycardia therapies include the above-cited U.S. Pat. No. 4,726,380 issued to Vollmann et al., above cited U.S. Pat. No. 4,587,970 issued to Holley et al., and U.S. Pat. No. 4,830,006 issued to Haluska, incorporated herein by reference in their entirety.

Figure 3:
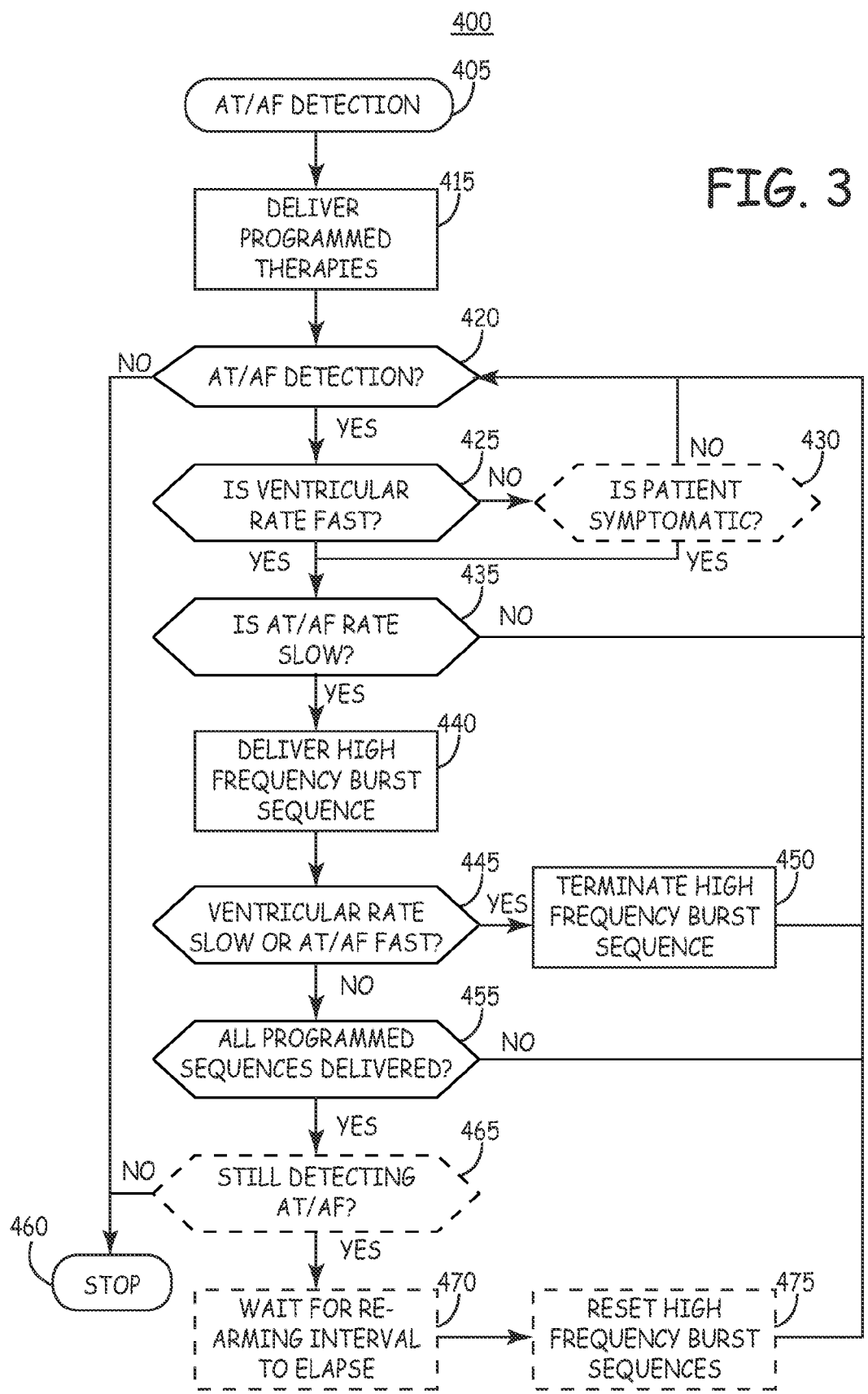
FIG. 3 is a flow diagram providing an overview of a method for controlling ventricular rate in the presence of a persistent atrial arrhythmia.

FIG. 3 is a flow diagram providing an overview of a method for controlling ventricular rate during persistent atrial arrhythmias in accordance with the present invention. Method 400 begins at step 405 when an atrial arrhythmia is detected. Atrial rhythm monitoring may be performed, as described above, based on EGM signal monitoring which typically involves measuring P—P intervals. Atrial arrhythmias are typically detected when a predetermined number of P—P intervals meet arrhythmia detection interval criteria.

Preferably, after detecting an atrial arrhythmia, an attempt is first made to terminate the atrial arrhythmia by delivering a programmed menu of therapies at step 415. For the purposes of the present invention, methods for detecting an atrial arrhythmia at step 405 and methods for delivering atrial arrhythmia therapies at step 415 may be performed according to methods known in the prior art. Programmed therapies may include anti-tachycardia pacing, high frequency burst pacing, cardioversion and/or defibrillation shocks. If AT/AF is not detected at decision step 420 after delivering programmed therapies at step 415, i.e., the arrhythmia is successfully converted to normal sinus rhythm, method 400 is terminated at step 460.

If, however, all programmed therapies have been exhausted and AT/AF is still detected at decision step 420, method 400 proceeds to decision step 425 to determine if ventricular rate control methods are needed. At step 425, method 400 determines if the ventricular rate is fast. This determination may be made based on a predetermined ventricular threshold rate which, if crossed, triggers ventricular rate control interventions. The ventricular threshold rate may be defined according to a predetermined number of R—R intervals shorter than a selected "fast" R—R interval. The ventricular threshold rate used for detecting a "fast" ventricular rate during an atrial arrhythmia may be slower than ventricular rates corresponding to ventricular tachycardia and ventricular fibrillation detection criteria. For example, a fast ventricular rate during a persistent AT/AF episode may be about 110 bpm or more and may vary between patients.

If the ventricular rate is determined to be "fast" at step 425, according to the predefined criteria, method 400 proceeds to step 435. If the ventricular rate is not determined to be fast, method 400 returns to step 420. As long as AT/AF continues to be detected at step 420, the ventricular rate will be monitored at step 425, either periodically or continuously, to determine if ventricular rate control is needed. If the AT/AF episode spontaneously terminates, method 400 is terminated at step 460.

An optional step 430 may be included for allowing a patient-triggered event marker to activate ventricular rate control intervention when the patient feels symptomatic, whether or not "fast" ventricular rate criteria are met. In other embodiments, ventricular rate control intervention activation may require both a "fast" ventricular rate and a patient-indicated symptomatic event. Using an external device, such as a patient activator or patient programmer, the patient may enter an event marker indicating that the patient feels symptomatic. Such an event marker may be stored in device 10 memory along with other arrhythmia episode data. If the currently detected atrial arrhythmia episode is marked as symptomatic at any time during the episode, ventricular rate control intervention may be invoked by proceeding to step 435. A patient activator that may be adapted for use with the present invention for marking an arrhythmia episode as symptomatic is generally disclosed in U.S. Pat. No. 5,987,356, issued to DeGroot, hereby incorporated herein by reference in its entirety. A patient programmer that may be adapted for use with the present invention is generally disclosed in U.S. Pat. No. 6,249,703, issued to Stanton, et al., hereby incorporated herein by reference in its entirety.

At decision step 435, method 400 verifies that the atrial rhythm is a relatively slow atrial arrhythmia. The benefits of slowing the ventricular rate by accelerating the atrial rate by delivering a stimulation therapy are expected to be realized when the atrial arrhythmia is initially occurring at a slow rate. If the atrial arrhythmia is already fast, the proposed ventricular rate control intervention is expected to be of little benefit. The atrial rate may be verified as slow at a step 435 according to a predetermined number of measured P—P intervals exceeding a predetermined minimum P—P interval. The predetermined minimum P—P interval will generally be shorter than the longest AT detection interval but may be shorter or longer than the longest AF detection interval since AT and AF detection interval zones may overlap.

Figure 4:
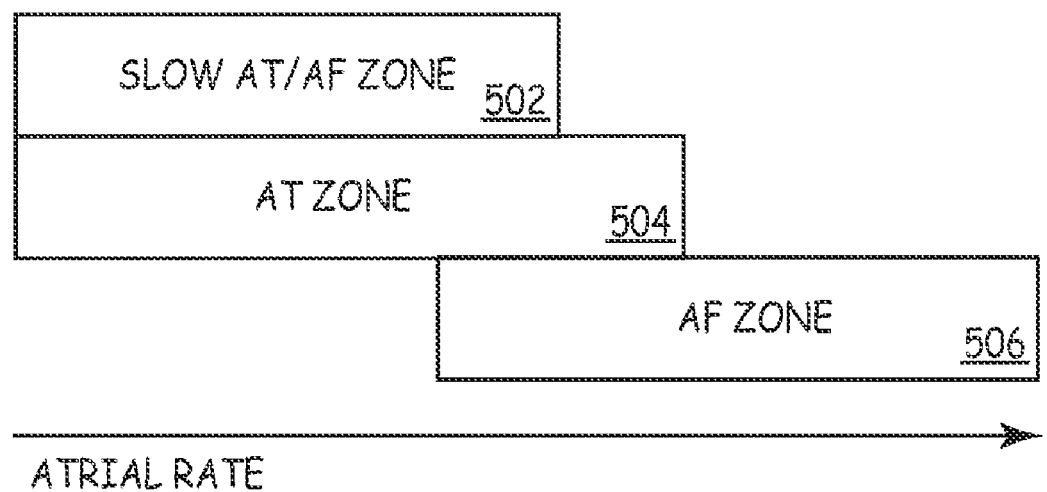
FIG. 4 is a diagram illustrating the relationship that may exist between atrial rate zones.

FIG. 4 is a diagram illustrating the relationship that may exist between the atrial rate zones. An AT detection zone 504 and an AF detection zone 506 may overlap. The "slow" atrial arrhythmia zone 502 may include a portion or all of the AT detection zone 504 and may include a portion of the AF zone 506.

If the atrial arrhythmia is not determined to be a "slow" arrhythmia, method 400 of FIG. 3 returns to step 420 to repeat the steps for monitoring for a fast ventricular rate and/or symptomatic episode coinciding with a "slow" atrial arrhythmia as long as the AT/AF episode is detected.

If the atrial arrhythmia is verified as a "slow" arrhythmia at decision step 435, high frequency burst pacing sequences are initiated at step 440. A programmable number of high frequency burst pacing sequences may be initiated. Each sequence may include a programmable duration or number of pacing pulses delivered at a high frequency, typically 50 Hz. For example, between 1 and 50 sequences that are 1 to 10 seconds in duration may be selected. Throughout the delivery of the high frequency burst pacing sequences, the ventricular and atrial rhythms are preferably monitored. If the ventricular rate slows, e.g., to a rate less than the fast ventricular threshold rate or another predefined acceptable rate, the burst pacing has been effective in controlling ventricular rate, and the delivery of remaining scheduled sequences may be suspended at step 450. If the atrial arrhythmia accelerates, such that the atrial arrhythmia rate no longer satisfies the "slow" arrhythmia criteria, burst pacing may be suspended at step 450.

Method 400 returns to step 420 to continue monitoring for conditions appropriate for ventricular rate control intervention and may deliver any remaining high frequency burst sequences if these conditions are met again during the detected AT/AF episode. Once all programmed sequences have been delivered, as determined at decision step 455, method 400 may be terminated at step 460.

Alternatively, as shown by optional steps 465 through 475 in FIG. 3, a re-arming of the ventricular rate control therapy may occur after a predetermined time interval if the atrial arrhythmia episode continues to be detected. After all programmed sequences have been delivered, as determined at decision step 455, method 400 verifies the AT/AF episode is still being detected at decision step 465. If the episode has terminated, method 400 is terminated at step 460. If the episode is continuing, method 400 waits a predetermined interval of time at step 470 after which the ventricular rate control intervention is re-armed at step 475 by re-setting the programmed number of burst pulse sequences. Method 400 then returns to step 420 to repeat steps 425 through 475 for delivering high frequency burst pacing as needed to control the ventricular rate during the sustained atrial arrhythmia episode.

Re-arming of the ventricular rate control intervention may occur during a sustained AT/AF episode associated with a fast ventricular rate after a specified interval of time has elapsed, as shown in FIG. 3. Re-arming of the ventricular rate control intervention may additionally or alternatively occur when a "fast" ventricular rate returns after it has been successfully slowed by burst pacing during a sustained AT/AF episode.

In some embodiments, future ventricular rate control interventions may be controlled based on the success of a previous intervention. For example, if high frequency burst pacing was found ineffective in slowing the ventricular rate during one or more sustained AT/AF episodes, method 400 may be automatically disabled such that future attempts of burst pacing do not occur. In other embodiments, if successful slowing of the ventricular rate occurs at one atrial rate but does not occur at another atrial rate, the "slow" atrial rate criterion may be automatically adjusted to allow ventricular rate control intervention to occur at the atrial rates known to be responsive to the ventricular rate control therapy. In a method for controlling the ventricular rate control therapy, therefore, a record of delivered therapies along with atrial rate and ventricular rate information may be stored and used in determining if ventricular rate control therapies are delivered in the future.

Some of the techniques described above may be embodied as a computer-readable medium comprising instructions for a programmable processor such as microprocessor 224 or pacer timing/control circuitry 212 shown in FIG. 2. The programmable processor may include one or more individual processors, which may act independently or in concert. A "computer-readable medium" includes but is not limited to any type of computer memory such as floppy disks, conventional hard disks, CR-ROMS, Flash ROMS, nonvolatile ROMS, RAM and a magnetic or optical storage medium. The medium may include instructions for causing a processor to perform any of the features described above for initiating a session of the escape rate variation according to the present invention.

Thus, a system and method have been described for controlling ventricular rate during persistent atrial arrhythmias using atrial high-frequency burst pacing. It is recognized that numerous modifications and variations of the embodiments described herein may be conceived by one having skill in the art and the benefit of the teachings provided herein. The embodiments described, therefore, are intended to be exemplary, not limiting, with regard to the following claims.

What is claimed is:

1. A medical device for delivering cardiac stimulation, comprising:
   a first electrode, positioned within a first chamber of a heart, sensing cardiac signals associated with the first chamber and capable of delivering stimulation to the first chamber;
   a second electrode, positioned within a second chamber of the heart, sensing cardiac signals associated with the second chamber and capable of delivering stimulation to the second chamber;
   a processing unit processing the sensed signals and controlling the stimulation delivery via the first electrode and the second electrode, the processing unit determining whether a predetermined rhythm is detected in the first chamber and delivering high-frequency burst pacing to the first chamber in response to a predetermined rate being sensed in the second chamber during the predetermined; and
   a patient signaling device generating a patient-generated signal, wherein the processing unit detects the patient-generated signal and delivers high-frequency burst pacing to the second chamber of the heart in response to the patient-generated signal.

2. The device of claim 1, wherein the processing unit sets a maximum rate for delivering the high-frequency burst pacing.

3. The device of claim 1, wherein the high-frequency burst pacing includes a sequence of a predetermined number of pulse bursts, each of the predetermined number of pulse bursts corresponding to a predetermined duration of time and a predetermined pulse frequency.

4. A medical device for delivering cardiac stimulation, comprising:
   a first electrode, positioned within a first chamber of a heart, sensing cardiac signals associated with the first chamber and capable of delivering stimulation to the first chamber;
   a second electrode, positioned within a second chamber of the heart, sensing cardiac signals associated with the second chamber and capable of delivering stimulation to the second chamber; and
   a processing unit processing the sensed signals and controlling the stimulation delivery via the first electrode and the second electrode, the processing unit determining whether a predetermined rhythm is detected in the first chamber and delivering high-frequency burst pacing to the first chamber in response to a predetermined rate being sensed in the second chamber during the predetermined rhythm, wherein the high-frequency burst pacing includes a sequence of a predetermined number of pulse bursts, each of the predetermined number of pulse bursts corresponding to a predetermined duration of time and a predetermined pulse frequency, and wherein the processing unit is programmed to suspend deliver of the high-frequency burst pacing in response to one of the predetermined rate being less than a first rate threshold and a rate associated with the first chamber being greater than a second rate threshold.

5. The device of claim 4, wherein the processing unit is programmed to deliver the remaining pulse burst of the suspended sequence of pulse bursts in response to one of the predetermined rate being greater than the first rate threshold and the rate associated with the first chamber being less than the second rate threshold.

6. The device of claim 5, wherein the processing unit is programmed to determine whether the predetermined rhythm is detected subsequent to the delivered sequence of a predetermined number of pulse bursts and resets the sequence of pulse bursts in response to the predetermined rhythm being subsequently detected.

7. A method for controlling delivery of cardiac stimulation by a medical device, comprising:
   sensing a predetermined rhythm in a first chamber of a heart;
   determining whether a predetermined rate is sensed in a second chamber of the heart during the sensed predetermined rhythm;
   delivering high-frequency burst pacing to the first chamber in response to the detected predetermined rate; and
   detecting a patient-generated signal and delivering high-frequency burst pacing to the second chamber of the heart in response to the patient-generated signal.

8. The method of claim 7, further comprising setting a maximum rate for delivering the high-frequency burst pacing.

9. A method for controlling delivery of cardiac stimulation by a medical device, comprising:
   sensing a predetermined rhythm in a first chamber of a heart;
   determining whether a predetermined rate is sensed in a second chamber of the heart during the sensed predetermined rhythm;
   delivering high-frequency burst pacing to the first chamber in response to the detected predetermined rate; and
   suspending the delivering in response to one of the predetermined rate being less than a first rate threshold and a rate associated with the first chamber being greater than a second rate threshold, wherein the high-frequency burst pacing includes a sequence of a predetermined number of pulse bursts, each of the predetermined number of pulse bursts corresponding to a predetermined duration of time and a predetermined pulse frequency.

10. The method of claim 9, further comprising delivering the remaining pulse burst of the suspended sequence of pulse bursts in response to one of the predetermined rate being greater than the first rate threshold and the rate associated with the first chamber being less than the second rate threshold.

11. The method of claim 10, further comprising:
   determining whether the predetermined rhythm is detected subsequent to the delivered sequence of a predetermined number of pulse bursts; and
   resetting the sequence of pulse bursts in response to the predetermined rhythm being subsequently detected.

12. A computer readable medium having computer executable instructions for performing a method comprising:
   sensing a predetermined rhythm in a first chamber of a heart;

determining whether a predetermined rate is sensed in a second chamber of the heart during the sensed predetermined rhythm;

delivering high-frequency burst pacing to the first chamber in response to the detected predetermined; and detecting a patient-generated signal and delivering high-frequency burst pacing to the second chamber of the heart in response to the patient-generated signal.

* * * * *